United States Patent [19]

Raymond et al.

[11] Patent Number: 4,571,543
[45] Date of Patent: Feb. 18, 1986

[54] SPECIFIC MATERIAL DETECTION AND MEASURING DEVICE

[75] Inventors: Leonard S. Raymond; Warren R. Jewett, both of Tucson, Ariz.

[73] Assignee: Southwest Medical Products, Inc., Tucson, Ariz.

[21] Appl. No.: 479,712

[22] Filed: Mar. 28, 1983

[51] Int. Cl.[4] ............................................. G01N 27/40
[52] U.S. Cl. ................. 324/425; 324/61 R; 357/25; 422/88; 422/98; 436/178
[58] Field of Search ........... 324/61 R, 450, 425, 324/439; 128/204.22; 361/278, 280, 284, 286, 315, 327, 313, 433; 357/25; 422/88, 90, 98; 436/151, 178

[56] References Cited

U.S. PATENT DOCUMENTS

| | | | |
|---|---|---|---|
| 3,873,927 | 3/1975 | Overall | 324/61 R |
| 3,950,980 | 4/1976 | Braun et al. | 422/83 |
| 3,999,122 | 12/1976 | Winstel et al. | 357/25 |
| 4,150,670 | 4/1979 | Jewett et al. | 128/204.22 |
| 4,302,530 | 11/1981 | Zemel | 357/25 |
| 4,324,761 | 4/1982 | Harris | 422/98 |
| 4,411,741 | 10/1983 | Janata | 357/25 |
| 4,446,474 | 5/1984 | Mizusaki et al. | 357/25 |

Primary Examiner—Ernest F. Karlsen
Assistant Examiner—Kevin D. O'Shea
Attorney, Agent, or Firm—J. Michael McClanahan

[57] ABSTRACT

A device for sensing the presence of and measuring the concentration of a specific non-aqueous particle or gas material in an environment, the device comprising an interdigitated capacitor having at least a pair of selected covering layers thereupon, said pair of layers comprising a first passive electrically insulative layer and a second material layer having a spacial relationship to said first layer, said second layer selectively permeable to the specific material to be sensed and measured; said second coating, when juxtaposed said first coating, selectively permitting permeability of the particular material sought to be sensed and measured, and when spaced apart, permitting passage through of the specific material in order that the material may migrate to the proximity of the first coating and thereby be sensed and measured. The presence of the specific material modifies the dielectric constant of the dielectric in the interdigitated capacitor electric field and thus the capacitor's capacitance, whereupon the interdigitated capacitor's capacitance is compared with a proximate temperature sensing interdigitated capacitor in a capacitance sensing circuit and by the change of the capacitance, the presence and concentration of the specific material determined.

18 Claims, 9 Drawing Figures

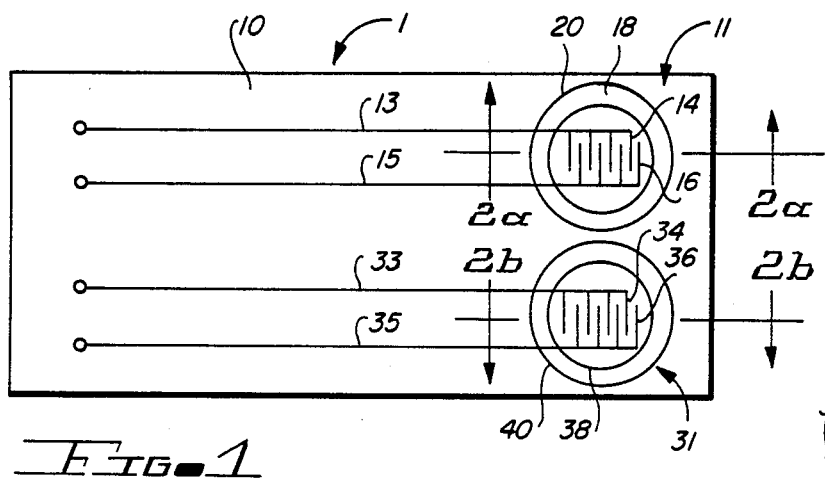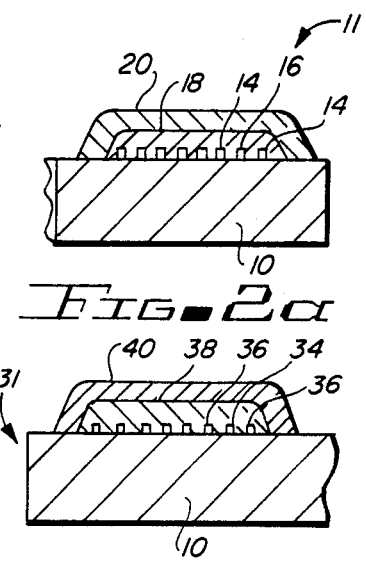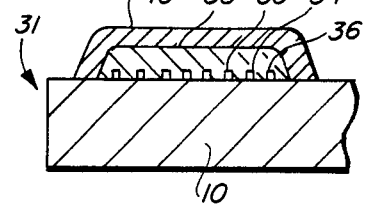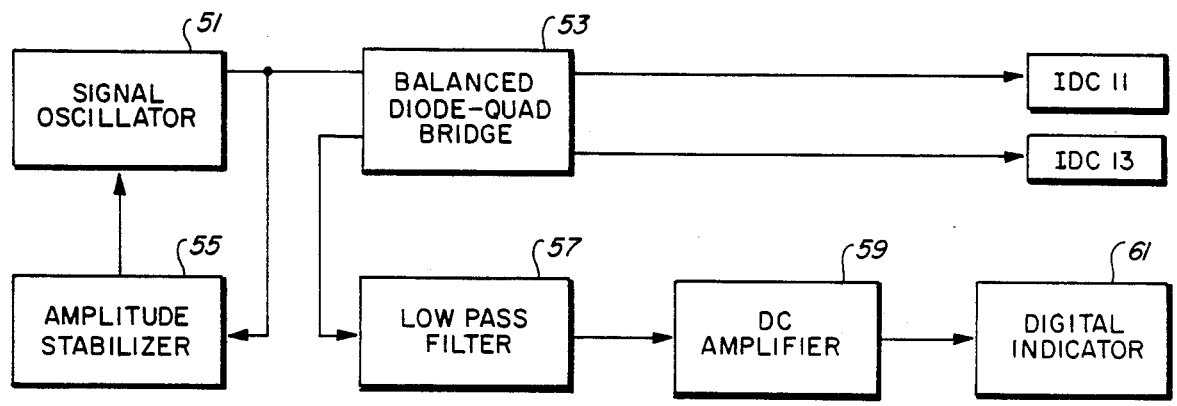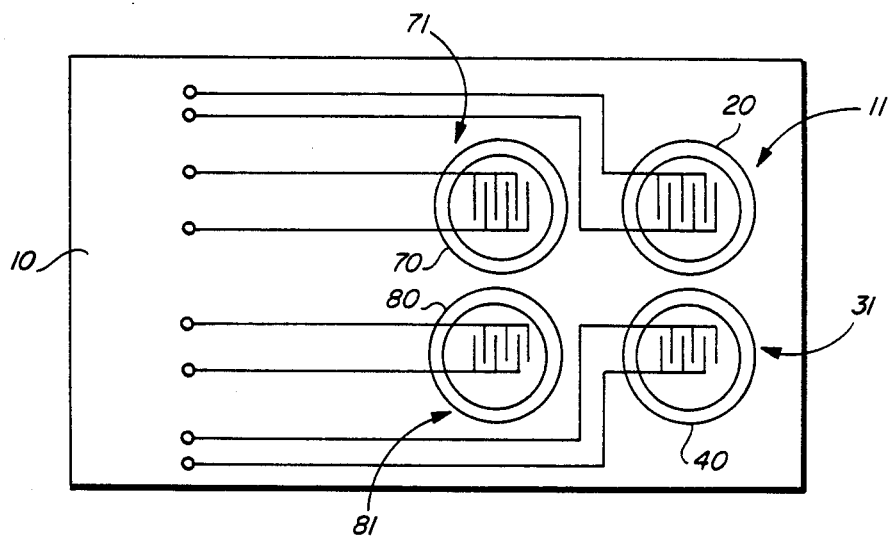

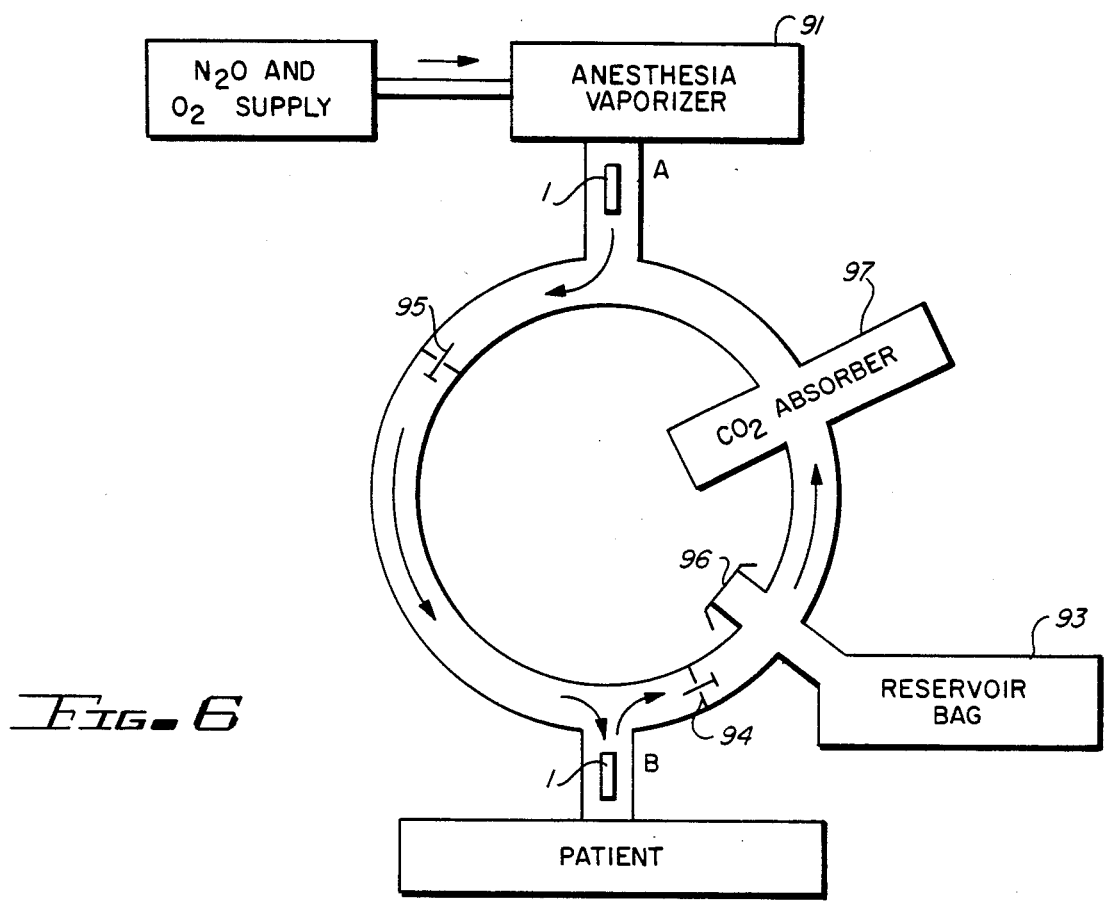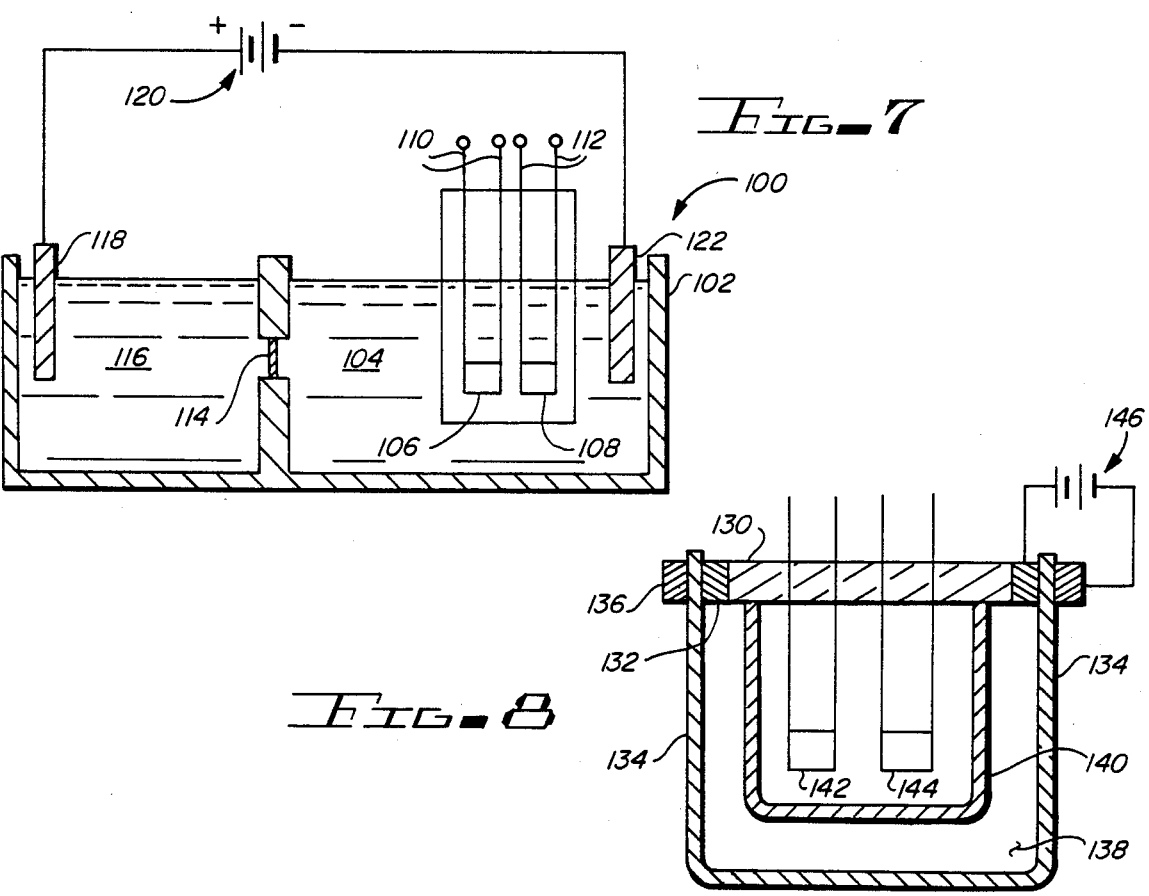

SPECIFIC MATERIAL DETECTION AND MEASURING DEVICE

BACKGROUND OF THE INVENTION

This invention relates to devices employing interdigitated capacitors for the detection and measurement of the concentration of selected non-aqueous fluids, i.e., gases and liquids, or specific non-aqueous materials or particles, i.e., ions, molecules, or the like in the presence of fluids.

Capacitors of the type having interdigitated plates or fingers have been known and are commonly available in the prior art. These devices have been used in various embodiments to indicate moisture in the atmosphere. For example, R. L. Stevens, et al. in U.S. Pat. No. 2,219,497 describes an electrostatic type test electrode having interdigitated finger-like electrodes covered by a layer of hydroscopic material adapted to absorb moisture from the air in a known relation to the relative humidity of the air. Stevens discloses several capacitor constructions including straight-line interdigitation and concentric circles attached to opposite electrodes placed upon a substrate.

Further, Suntola, in U.S. Pat. No. 4,164,868, describes a capacitive type humidity transducer having a pair of electrically conductive coatings spaced from each other with a dielectric film having water absorption characteristics covering portions of the electrically conductive coatings. Thereafter, an outer electrically conductive, water-permeable layer is carried by the dielectric film covering the electrically conductive coatings which comprise the capacitor plates.

In Suntola, the resultant change in capacitance measured between the plates of the capacitor as modified by the water absorption film is detected by incorporation of the capacitive humidity transducer into a suitable electrical circuit providing measurement of the capacitance and change in capacitance.

Example of suitable electrical circuits to measure capacitance of capacitance type transducers are known in the field, for example, in *Review of Scientific Instruments*, Volume 44, No. 10, October 1973, authors Dean R. Harrison and John Dimeff illustrate a diode-quad type bridge circuit for use with capacitance transducers wherein a very accurate method of measuring capacitance of an unknown capacitor is provided by placing the unknown capacitor in the diode-quad bridge circuit in series with known capacitors and in parallel to a voltage frequency source. The output voltage of the diode-quad bridge circuit, with a stabilized input voltage frequency source, is a DC voltage which is a function of the difference between the capacitance sought to be measured and the capacitance of the known capacitor.

SUMMARY OF THE INVENTION

The present invention comprises means by which the presence and concentration of certain specific non-aqueous chemicals, compounds, materials, gases, liquids or the like may be detected and measured in the environment in which the material sought to be detected resides.

Such detection and concentration measurement is taken while placing the device in the environment in which the material to be detected is believed to reside. To accomplish the above, Applicant's device provides means by which the particular material to be detected is permitted to collect around and in the electric field of the device, to the exclusion of other chemicals, gases, or the like which may be in the environment, and by the fact of collection and rate of collection, presence and concentration is determined. More specifically, selected membrane coatings on the interdigitated capacitors which absorb or permit the passage of the particular material or particle into the interior of or through the membrane are utilized. By such permeation of the selected fluid or particle into or through the membrane, the dielectric constant of the dielectric in the electric field between the plates of an interdigitated capacitor of which the membrane is a part is affected resulting in a change in capacitance of the interdigitated capacitor, all due to the presence of the selected fluid or particle. Such change in capacitance is then detected and measured.

In a basic embodiment of the device, electrically conductive strips of metal are placed upon an insulative substrate to form two capacitor plates, the plates having a configuration of interdigitated fingers, concentric circles, intertwined spirals, or the like. Electrical leads for connection to ancilliary equipment attach in turn to each plate. Next, an electrically insulative coating of an appropriate material covers the electrically conductive capacitor plates and leads, this insulative covering being chosen to be completely passive, non-reactive, and non-absorptive to the specific material sought to be detected and to other chemicals and materials present in the surrounding environment.

Following the insulative passive covering of the electrical strips and leads is a second layer of a selected membrane or the like. This second layer membrane may be a coating immediately covering the first insulative passive layer or it may be spaced apart from the insulative passive layer, in which case, there may be an intermediate medium, substantially non-reactive, such as a gas or liquid, interposed between the first insulative layer covering and the second layer membrane. The second layer membrane has a known relationship with the specific material to be detected, whether it be selectively absorptive, selectively porous, or possess some other selective physical property.

In the process of utilizing Applicant's device, the specific material to be detected enters or passes the second layer to the immediate proximity of the first layer and thereby shows its presence by affecting the dielectric constant of the material within the electric field between the plates of the interdigitated capacitor.

The device is then connected into an external electrical circuit which enables the resulting change in capacitance of the interdigitated capacitor to be detected and measured. In the preferred embodiment, the subject interdigitated capacitor detection device is placed into a diode-quad capacitance measuring electrical circuit, which circuit impresses a voltage of known frequency and magnitude across the plates of the interdigitated capacitive detection device, and of a similarly constructed, proximate interdigitated capacitive device which, however, has been completely passivated by a totally non-reactive second layer or does not react with the environment. This permits the second, or passivated interdigitated capacitor to sense temperature of the environment. The change in capacitance between the two interdigitated capacitors is detected while both are situated in the same environment The magnitude of a dc voltage output of the electrical circuit is indicative of the differential change in the capacitance between the two interdigitated capacitors. Such differential change in capacitance and rate of change of capacitance is reflective of the amount of the specific material which has entered into, become collected, or passed the second membrane layer to enter into the electric field between the capacitor plates, change the constant of the dielectric of the interdigitated capacitor, and thus the capacitor's capacitance.

For example, for the detection of a halogenated hydrocarbon or nitrous oxide type anesthesia gas, the second layer comprises a specified type of a silicone rubber membrane layer immediately covering the first insulative layer, which silicone rubber layer selectively admits the particular anesthesia gas at a known rate relative to concentration into molecular size interstices in the silicone rubber.

When, however, the device is used as an ion detection and measuring system, the second layer comprises a membrane spaced from the first insulative layer, which second layer membrane permits the passage of the selected ion into the proximity of the interdigitated capacitor. For example, if it is desired to detect Potassium ions in a solution, the interdigitated capacitor is first surrounded by deionized water which in turn is separated from the solution containing the Potassium ions by the second layer membrane acting as a barrier to all but the selected ion, including the deionized water. This membrane is permeated by the Potassium ions which enter the deionized water environment of the interdigitated capacitor to differentially change its capacitance.

The temperature sensing interdigitated capacitor with which the specific material sensing interdigitated capacitor is compared is covered with a second layer material which matches or is reflective of the effect of temperature upon the sensing interdigitated capacitor second layer material. This layer, of course, must be impervious or made impervious to the environment, including the gas or particle desired to be sensed. In the preferred embodiment, the non-reactive material covered temperature sensing interdigitated capacitor is adjacent to the active sensing interdigitated capacitor, easily made so by placing both interdigitated capacitors upon the same substrate.

It is obvious that other examples of specific materials for the sensing interdigitated capacitors' second layers may be devised for broad applications of Applicant's device.

It is an object of the subject device to provide a device by which specific non-aqueous chemicals, gases, ions, or the like, may be sensed in the environment in which they are expected to reside.

It is another object of the subject invention to provide a means by which the concentration of a specific non-aqueous material in an environment may be determined.

It is further an object of the subject invention to provide a detection means of an interdigitated capacitor covered by an insulative passive coating, and a second layer permeable to a particular gas, liquid, or other material.

It is still further another object of the subject invention to provide a specific substance detection and level measuring device wherein the device comprises in part, a material permitting the passage of detectable selected molecules into its interior.

Other objects of the invention will in part be obvious and will in part appear hereinafter. The invention accordingly comprises the apparatus possessing the construction, combination of elements, and arrangement of parts which are exemplified in the following detailed disclosure and the scope of the Application of which will be indicated in the claims.

BRIEF DESCRIPTION OF THE DRAWINGS

For further understanding of the nature and objects of the present invention, reference should be had to the following detailed description taken in connection with the accompanying drawings wherein:

FIG. 1 is a top view of the apparatus for detecting and measuring concentration of a specific gas;

FIGS. 2a and 2b are cross-sectional views taken along lines 2a—2a and 2b—2b of the apparatus shown in FIG. 1;

FIG. 3 is a block schematic diagram of the electronics circuitry utilized in the preferred embodiment of the invention;

FIG. 4 is a top view of an alternate embodiment of the subject device;

FIG. 6 is a block schematic diagram employing the invention in a typical anesthesia process system;

FIG. 7 is a cross-sectional view of the invention in a specific ion-detection configuration; and FIG. 8 is a cross-sectional view of the invention in an alternate specific ion detection configuration.

FIG. 9 is a cross-sectional view of the invention with the temperature sensing interdigitated capacitor modified.

In the various views, like index numbers refer to like elements.

DETAILED DESCRIPTION OF THE PREFERRED EMBODIMENT

Figure 5:
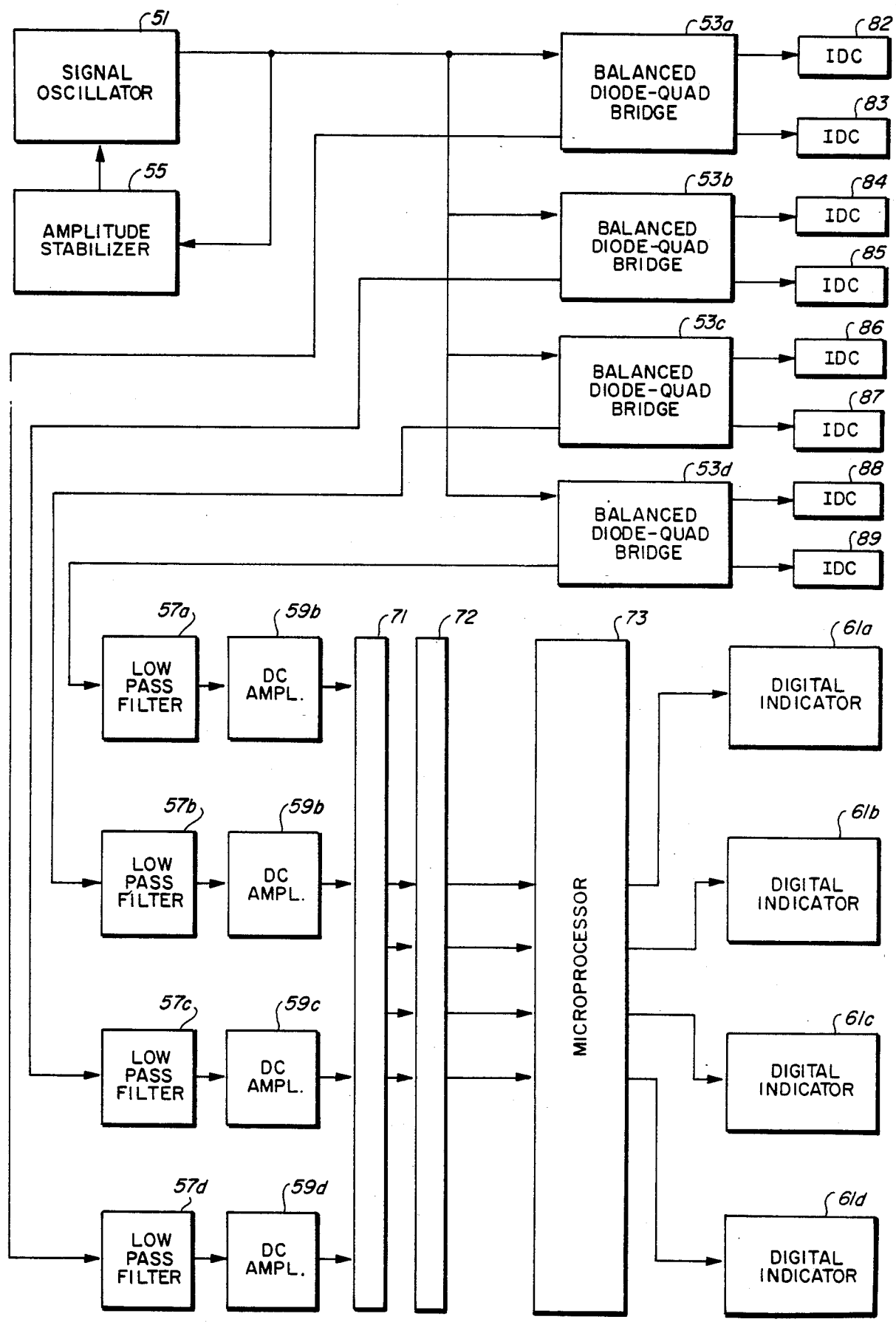
FIG. 5 is a block schematic diagram of the electronic circuitry for utilizing multiple material detection apparatus.

Referring now to FIG. 1, a top view of the apparatus 1 for detecting and measuring concentration of a non-aqueous specific material is shown. Firstly, two interdigitated capacitors 11 and 31 are situated on an electrically insulating substrate 10. From left to right, the interdigitated capacitor 11 comprises two elongated connecting leads 13 and 15 terminating at a matrix of interdigitated fingers 14 and 16. The matrix formed by the interdigitated fingers may be selectively varied as desired with variables such as finger lengths, finger widths, spacing between adjacent fingers, and the thickness which the finger rises above the substrate, i.e., out of the drawing (perpendicular to the plane of the drawing), including additional geometries, i.e., two fingers tracing an inward spiraling pattern, or two fingers tracing a rectangular or square pattern, or the like.

In FIG. 1, interdigitated capacitor 31 is similarily constructed as interdigitated capacitor 11, having two elongated connecting leads 33 and 35 terminating at a matrix of interdigitated fingers 34 and 36.

It is anticipated, though not required, that similar dimensions will be applied to different interdigitated capacitors situated on a single substrate.

The leads connecting interdigitated capacitor 11 and 31 extend in the preferred embodiment a substantial distance (relative to size) from the interdigitated capacitors to a point where they may be electrically connected to other portions of the electrical circuitry hereinafter described.

The substrate 10 utilized has the characteristic of being a good electrical insulator as well as having structural integrity and in this respect, glass, sapphire, or other similar substance may be used. The interdigitated capacitor may be placed upon the substrate by many methods and in the preferred embodiment, the Applicants etched away unwanted portions of metal vapor previously deposited upon the substate. In this case, tungsten was the electrically conductive metal utilized for the interdigitated capacitor although it is anticipated that other types of electrically conductive materials could be used, such as aluminum or other like metals.

In embodiments which have been constructed by the Inventors, typical dimensions of the interdigitated capacitor were five mils (0.127 mm) width on the interconnecting leads 13 and 15, fingers 14 and 16 widths of 1 mil (0.0254 mm), 1 mil (0.0254 mm), spacing between adjacent fingers, and 100 to 160 mils (2.54 to 4.064 mm) separation between interconnecting leads 13 and 15. Thickness of the interdigitated fingers in a direction perpendicular to the plane of the substrate was 2500 angstroms, although this was varied in different embodiments from 2500 to 10,000 angstroms. The substrate chosen, made of sapphire, was ½ inch (12.7 mm) wide, 1 inch (12.7 mm) long, and 0.018 inch (0.457 mm) thick.

The outline of the material coatings covering the interdigitated capacitors 11 and 31, are represented by concentric circles 18 and 20, and 38 and 40 respectively. For purposes of presenting construction of the interdigitated capacitors, these coatings are represented as transparent, although this is not necessarily the case. The coatings are further detailed in the discussion of FIGS. 2a and 2b below.

Referring now to FIGS. 2a and 2b, cross-sectional views are detailed taken along lines 2a—2a and 2b—2b of the interdigitated capacitors 11 and 31 shown in FIG. 1. Forming a base is the substrate 10 having a relative thickness much greater than that of the interdigitated capacitors 11 and 31. Shown in interdigitated capacitors 11 and 31 respectively, are the end views of each of the interdigitated fingers of each capacitor, namely cross-sectional view of fingers 14 and 16, and fingers 34 and 36 respectively. Each of the interdigitated capacitors has two serial coverings, the first coverings 18 and 38 on the respective capacitors being a substance which is electrically insulative, has good adherence characterisitics, and is passive to the environment that the interdigitated capacitor is expected to come in contact with. Examples of such materials are silicon nitride and silicon oxide. In the preferred embodiment, silicon nitride was utilized for these first coatings 18 and 38 of the interdigitated capacitors. It is obvious that there are a large variety of compounds which may be utilized for the first coating in addition to silicon nitride, such as silicon oxide and aluminum oxide, or other materials and compounds having the requisite properties. The silicon nitride coatings 18 and 38 in the preferred embodiment were placed upon the interdigitated capacitor and substrate by low pressure chemical vapor deposition.

In the event that a layer of silicon oxide is chosen as the first coating insulative layer, such layer may be applied to the interdigitated capacitor upon the substrate by chemical vapor deposition, by sputtering, by evaporation, or by spinning on of an organic silicon compound which is then oxidized, all known common methods.

Still other organic silicon compounds such as silanes may be utilized for the first coating. These are placed on the interdigitated capacitor, spun in a centrifuge to produce a sufficiently thin coat, and then placed in an oven for curing. It has been determined that it is important to fix the thickness of the first insulative coating above the interdigitated capacitor 11 and 31, and that the thickness of the coating be approximately the same on both interdigitated capacitors.

Following the insulating layer is the second covering coatings or layers 20 and 40 on interdigitated capacitors 11 and 31 respectively. These coatings, in the preferred embodiment are of a different material than the first layer and may be different from each other, depending on what the particular function of the respective interdigitated capacitor is to be. Since the function of interdigitated capacitor 31 is to provide a temperature compensating and comparison capacitance to interdigitated capacitor 11 as later discussed, it is important that the two interdigitated capacitors have similar thermal characteristics.

In one embodiment, the invention is adapted for sensing the presence and concentration of a specific gas, such as one of the halogenated hydrocarbon gases commonly used in anesthesia. In the case of a halogenated hydrocarbon such as halothane, layer 20 of interdigitated capacitor 11 comprises a compound such as a silicone rubber, a specific example of which is Dow Corning Silicone Rubber DSR 517. The silicone rubber coating forms a membrane which in the presence of particular halogenated hydrocarbon gases, swells or expands. The swelling of silicone rubber in the presence of certain gases is a well recognized phenomenon. Silicone rubber is highly permeable by many gases, but not all of these cause swelling. Permeability is the product of diffusivity and solubility. It is assumed that the solubility aspect of the halogenated hydrocarbon gases in silicone rubber results in the swelling phenomenon. Thus the membrane exhibits characteristics of exclusivity. The material chosen for the second coating must be tailored to the specific gas to be detected.

The use of the term permeable throughout this application means more than to penetrate. It can in some cases include solubility of the selected material into the membrane, as well as penetration into the membrane or passage through the membrane. It is believed that the operative mechanism is purely physical—that it is due to the permeation of the matrix of the membrane by the chemical or material to be detected, and that the mechanism is reversible when the specific material's presence is removed.

Through the choice of the silicone rubber membrane utilized, a specific halogenated hydrocarbon molecule passes into the silicone rubber, entering between the molecules of the silicone rubber to become interspersed under the top surface. This causes the silicone rubber coating on the interdigitated capacitor to expand. The absorption relationship between the silicone rubber and the halogenated hydrocarbon builds up until an equilibrium is reached with the surrounding gas of which the halogenated hydrocarbon is a constituent. At that time, as many molecules of the halogenated hydrocarbon are leaving the silicone rubber layer as are entering, and the number of gas molecules which have entered the silicone rubber compound are directly proportional to the concentration of the halogenated hydrocarbon in the surrounding environment.

Since the second coating, along with the passivated first coating, constitutes the dielectric within the electric field of the interdigitated capacitor, change in the second coating results in changes in the capacitor capacitance. By the introduction of the gas molecules into the second coating, the dielectric of the material in the electric field of the interdigitated capacitor is changed resulting in a change in capacitance which is detected and measured as hereinafter explained.

Many elastomer and lipid substances, such as butyl rubber, polyurethane rubber, and fatty acid esters, have the characteristics permitting the entrance of halogenated hydrocarbons into these compounds, and may be substituted for the silicone rubber.

It is also noted that there are other compounds such as certain polymers and cellulose acetate which may be used as the second coating 20 and which act as permeability membranes to fluids, both gases and liquids, permitting constituents of the fluid to selectively burrow or penetrate into the membrane and changing the dielectric constant of the membrane coating.

Selectively as used through this application means that the membranes, or layer which is selective, discriminates between the material to be detected and some other materials which are present in the environment.

Considering now interdigitated capacitor 31 of FIG. 2b., the second coating 40 comprises a coating which will exhibit an effect upon interdigitated capacitor 31 to match the effect of temperature upon interdigitated capacitor 11. The most obvious coating then would be the same as the coating 20 on interdigitated capacitor 11, providing of course, that the coating 40 be modified such that it is nonresponsive to the environment other than to reflect change in temperature. Such modification is accomplished by placing a non-reactive barrier between the environment and second coating 40, the barrier being substantially out of the electric field of the interdigitated capacitor. A thin sheet of glass (not shown) was selected, the glass so sized that it extended well beyond the finger interdigitation such that the fringe of second coating 40 exposed to the environment below the glass plate is well beyond any measurable part of the electric field.

As a consequence, this interdigitated capacitor is only sensitive to changes in temperature and thus provides a temperature reference for comparison with the first interdigitated capacitor 11.

The silicone rubber second coating 20 and 40 of the interdigitated capacitor 11 and 31 in the preferred embodiment is placed upon the first coating 18 and 38 by an eye-dropper, by brushing on, painting on, gluing, or other appropriate means. Layer 20 is allowed to dry, cure, or set in accordance with its normal application procedure. The glass plate 42 is placed upon second coating 40 permitting its adherence thereto and the coating 40 then is also permitted to dry, cure, or set in accordance with normal procedures. As with the first layers, the thickness of the second layers are important because of their effect on the capacitance of the interdigitated capacitor. Thicknesses of all layers are thus monitored by applying each layer in known amounts of material.

Referring now to FIG. 3, a block schematic diagram of the electronic circuitry utilized to sense changes in capacitance of the interdigitated capacitors is shown. As indicated in FIG. 3, a signal oscillator 51 generates the carrier signal which is directed to the balanced diode-quad bridge 53 of which the interdigitated capacitor 11 occupies one leg and interdigitated capacitor 31 occupies another leg. Tests have indicated that the frequency of the carrier is not critical as satisfactory results have been obtained for frequencies in the range of 50 KHz to 12 MHz. The output of the oscillator 51 is fed back into a amplitude stabilizer 55 which regulates the oscillator to insure that the carrier signal amplitude is constant. The output of the balanced diode-quad bridge 53 is directed into the low-pass filter 57 which blocks the carrier signal and outputs to the DC amplifier 59 a slowly varying DC signal, the voltage amplitude of the DC signal being indicative of the difference between the capacitance of interdigitated capacitor 11 and interdigitated capacitor 31. The output of the DC amplifier 59 is then directed to digital voltage indicator 61 which, in the preferred embodiment, gives a visual presentation of the amplified DC signal, indicative of the change difference in capacitance.

Substantially, the electronic circuitry represented by the schematic block diagram in FIG. 3 is shown in a paper by Dean R. Harrison and John Dimeff in an article entitled, "A Diode Quad Bridge Circuit For Use With Capacitance Transducers", Ames Research Center, NASA, Moffett Field, Calif. 94035, *Rev. Sci. Instrum.*, Vol. 44, No. 10, October 1973. Circuit design and modifications for specific purposes were made by the Applicants from the circuits shown in the above article and are within the present state of the art. As is obvious, any electronic circuit in which changes in capacitance varies an output may be utilized, such as well known RC timing circuits or frequency dependent tuning circuits.

As indicated above, when the subject device is inserted into an environment consisting of the specific gas to be detected and concentration measured, the passage of the specific gas into the second coating 20 on interdigitated capacitor 11 affects the dielectric constant and thereby the capacitance of the interdigitated capacitor. The capacitance of interdigitated capacitor 31 is only affected by change in temperature of the environment and serves as a reference capacitor and correction factor for change due to temperature effect upon the gas sensing interdigitated capacitor 11. Thus as the temperature of both capacitors move along a parallel path, relative to temperature, the difference voltage sensed, amplified, and displayed on a digital indicator 61 will be reflective of only the change in capacitance of interdigitated capacitor 11 due to changes caused by the specific gas permeation into the outer coating 20.

Tests were conducted of the device of the preferred embodiment wherein the interdigitated capacitors 11 and 31 had the dimensions which have been previously indicated, the first material coating on each comprising silicon nitride of a thickness of approximately 3500 Angstroms, and the second coating on each interdigitated capacitor comprising a thin coating of Dow Corning brand Silastic Medical Adhesive Type A silicone rubber, Catalog No. 891, applied by first mixing with toluene, 50% each by weight. "Silastic" is a registered trademark of the Dow Corning Corporation, Midland, Mich. One drop of the thinned silicone rubber was dropped on each interdigitated capacitor and then the mixture was wiped across and off the substrate. The substrate was then shaken to remove any excess silicone rubber. Over interdigitated capacitator 31 which was to be used for temperature compensation was placed a piece of microscope cover plate glass (0.006 inches (0.152 mm) thick) with the glass plate extending substantially beyond the fingers of the interdigitated capacitor. The substrate with the two interdigitated capacitors thereon was placed into a bell jar and a vacuum pulled for one-half hour to assist in out-gasing air and toluene from the silicone rubber. Thereafter, the silicone rubber was allowed to set for three hours in a box filled with dry nitrogen. The size of the glass plate was such that the fringe of the silicone rubber immediately below the glass plate exposed to the environment was sufficiently far removed from the interdigitated capacitor 31 that any environment which may be absorbed by the silicone rubber was not close enough to the field of interdigitated capacitor 31 as to affect its capacitance.

The tests were conducted by placing the subject device in the electrical circuit shown by the block schematic diagram of FIG. 3 with the subject device in a stream of air and a halogenated hydrocarbon (Halothane) added by means of an anesthesia vaporizer. Prior to the start of the tests, the voltage output of the preferred embodiment was placed to near zero on the digital indicator 61 by means of a voltage additive circuit opposing the output of dc amplifier 59. This set a reference for the device being in the presence of dry air. The carrier frequency was set at 1 MHz.

| Gas | Output |
|---|---|
| TEST 1. Temperature 4° C. | |
| Air | 0.06 mV |
| 3% Halothane | 9.62 mV |
| Air | 0.06 mV |
| TEST 2. Temperature 34° C. | |
| Air | 0.06 mV |
| 3% Halothane | 9.62 mV |
| Air | 0.06 mV |
| TEST 3. Temperature 34° C. | |
| Air | 0.06 mV |
| 1% Halothane | 3.21 mV |
| Air | 0.06 mV |
| 2% Halothane | 4.81 mV |
| Air | 0.06 mV |
| 3% Halothane | 9.62 mV |
| Air | 0.06 mV |

In all tests, rise time between the 10 to 90% points was approximately one-half second. There was full settling in 1.5 seconds. Fall time between the 10 to 90% points was approximately 0.9 seconds, with full settling in 1.5 seconds.

In addition, embodiments of the device utilizing an epoxy, such as DURO LOCTITE E-POX-E5, covering the silicon nitride first layer on the temperature sensing interdigitated capacitor 31 was also performed. "E-POX-E5" is a registered trademark of the Loctite Corporation, Cleveland, Ohio. In these embodiments, a different silicone rubber was utilized, namely General Electric Rubber Type RTV 615A, which was placed as a second layer on interdigitated capacitor 11 in a thickness of approximately 0.003 inch (0.076 mm).

Here tests were conducted by placing the subject device in a stream of air and different halogenated hydrocarbons added by means of an anesthesia vaporizer. Prior to the start of the tests, the device of the preferred embodiment was zeroed on the digital indicator so that no capacitance difference showed between the two interdigitated capacitors. A selected percent of the halogenated hydrocarbons was added by the operator into the airstream and in separate tests, 15 seconds (Test 1) and 30 seconds (Test 2) were allowed for the subject devices to settle in. In Test 1 after each reading was taken for one concentration, the vaporizer placing the halogenated hydrocarbon into the airstream was adjusted to no input of halogenated hydrocarbons into the airstream, at which time, and after 15 seconds had elapsed, the reading was again taken. In Test 2, a digital voltmeter was placed upon the output of the low frequency filter prior to the DC amplifier and the readings taken. The amplifier amplifies the voltage input by a constant 26.59 to indicate a voltage reading and the reading for zero percentage halogenated hydrocarbon is adjusted to zero on the output of the amplifier. Tests were run in Test 2 on two different devices simultaneously.

| Percent Halothane | Digital Indicator Reading | Percent Halothane | Detector No. 1 (MV) | Normalized Digital Indicator Reading | Detector No. 2 (MV) | Normalized Digital Indicator Reading |
|---|---|---|---|---|---|---|
| 0 | 0.00 | 0 | 11.2 | 0 | 8.2 | 0 |
| 1 | −0.60 | 1 | 48.8 | 1.00 | 48.1 | 1.06 |
| 0 | 0.00 | 2 | 86.4 | 2.00 | 88.1 | 2.12 |
| 2 | −1.15 | 3 | 124.1 | 3.00 | 128.1 | 3.19 |
| 0 | 0.00 | 2 | 86.5 | 2.00 | 88.1 | 2.12 |
| 3 | −1.64 | 1 | 48.9 | 1.00 | 48.1 | 1.06 |
| 0 | 0.00 | 2 | 86.5 | 2.00 | 88.1 | 2.12 |
| 3 | −1.60 | 3 | 124.1 | 3.00 | 128.1 | 3.19 |
| 0 | 0.00 | 2 | 86.5 | 2.00 | 88.1 | 2.12 |
| 2 | −1.07 | 1 | 48.9 | 1.00 | 48.1 | 1.06 |
| 0 | 0.00 | 0 | 11.2 | 0 | 8.1 | −0.27 |
| 1 | −0.52 | 3 | 124.0 | 3.00 | 128.1 | 3.10 |
| 0 | 0.00 | 0 | 11.2 | 0 | 8.1 | −0.27 |
| 2 | −1.03 | 3 | 124.0 | 3.00 | 128.2 | 3.10 |
| 0 | −0.01 | 0 | 11.2 | 0 | 8.2 | 0 |
| 3 | −1.63 | | | | | |
| 0 | 0.00 | | | | | |
| 3 | −1.63 | | | | | |
| 0 | 0.00 | | | | | |
| 2 | −1.10 | | | | | |
| 0 | −0.02 | | | | | |
| 1 | −0.58 | | | | | |
| 0 | −0.02 | | | | | |

In addition, tests were performed for different halothane concentrations at different flow rates. In these tests, the digital indicator reading was calibrated at 3.00 for halothane in a known concentration of 3%. Here, each reading was taken 15 seconds after stabilization.

In addition, other gases then halogenated hydrocarbons were also permitted to flow past the sensor and the digital indicator reading taken. In these cases, there was no movement of the digital indicator reading other than what is indicated and time was not necessary for stabilization. These results appear in Tests 4, 5, and 6, as follows:

| Percent Halothane | Flow Rate | Digital Indicator Reading | | Flow Rate | Digital Indicator Reading |
|---|---|---|---|---|---|
| | | | | TEST 4. | |
| | | | Percent Nitrous Oxide | | |
| | TEST 3. | | | | |
| 0 | 5 l/min | 0.00 | 0 | 5 l/min | 0.00 |
| 1 | ↑ | 1.00 | 16.7 | 6 l/min | 0.00 |
| 2 | ↑ | 2.00 | 28.0 | 7 l/min | 0.00 |
| 3 | ↑ | 3.01 | 37.5 | 8 l/min | 0.00 |
| 0 | ↑ | 0.01 | 0 | 5 l/min | 0.00 |
| 3 | ↑ | 3.00 | | | |
| 0 | ↑ | 0.01 | | | |
| 1 | ↓ | 1.01 | | TEST 5. | |
| 0 | ↓ | 0.01 | | | |
| 3 | ↓ | 3.00 | Percent Carbon Dioxide | | |
| 0 | ↓ | 0.00 | | | |
| 5 | ↓ | 5.01 | | | |
| 0 | 5 l/min | 0.00 | 0 | 5 l/min | 0.00 |
| | | | 16.7 | 6 l/min | 0.00 |

-continued

| Percent Halo-thane | Flow Rate | Digital Indicator Reading | Flow Rate | Digital Indicator Reading |
|---|---|---|---|---|
| 0 | 2 l/min | 0.00 | 28.0 | 0.00 |
| 3 | ↑ | 3.01 | 37.5 | 0.01 |
| 0 | ↑ | 0.00 | 0 | 0.01 |
| 3 | ↓ | 2.99 | | |
| 0 | 2 l/min | 0.00 | | |
| 0 | 10 l/min | 0.00 | TEST 6. | |
| 3 | ↑ | 2.99 | Percent Helium | |
| 0 | ↑ | −0.01 | | |
| 3 | ↑ | 2.99 | 0 | 5 l/min | −0.01 |
| 0 | ↑ | −0.01 | 16.7 | 6 l/min | −0.01 |
| 1 | ↓ | 1.00 | 28.0 | 7 l/min | −0.01 |
| 2 | ↓ | 2.01 | 37.5 | 8 l/min | −0.01 |
| 3 | ↓ | 3.01 | 0 | 5 l/min | −0.01 |
| 0 | 10 l/min | 0.01 | | |

Further tests were conducted with the same constants as were used in Test 1., only ethrane was substituted for halothane. Results of this test are shown below:

TEST 7.

| Percent Ethrane | Digital Indicator Reading |
|---|---|
| 0 | 0.00 |
| 1 | −0.47 |
| 0 | 0.00 |
| 2 | −0.83 |
| 0 | 0.00 |
| 3 | −1.03 |
| 0 | 0.00 |
| 3 | −0.97 |
| 0 | 0.00 |
| 2 | −0.78 |
| 0 | 0.00 |
| 1 | −0.45 |
| 0 | 0.00 |
| 2 | −0.80 |
| 0 | −0.02 |
| 3 | −1.00 |
| 0 | −0.03 |
| 3 | −0.99 |
| 0 | −0.04 |
| 2 | −0.79 |
| 0 | −0.04 |
| 1 | −0.46 |
| 0 | −0.06 |

It is noted that during the tests conducted by the Applicants, the results observed on the digital voltmeters did advance to the proximity of the readings which are recorded almost instantaneously after the halogenated hydrocarbons reached the interdigitated capacitors. A similar effect is shown in the results of the authors of an article appearing in the June, 1981 issue of the IEEE Transactions on Biomedical Engineering Vol. BME-28, No. 6 at Page 459 entitled *Piezoelectric Sorption Anesthetic Sensor,* wherein a piezoelectric crystal was coated with different types of silicone rubber and frequency change in the crystal was observed for the reaction of halogenated hydrocarbons in silicone rubber. The coated crystal was placed in the flow path of halogenated hydrocarbons in oxygen. Stepwise changes in gas concentrations were reflected in almost instantaneous change in the crystal frequency change. Rise time in the order of 1/10th. second was observed for the observed crystal frequency shift to reach 63% of its final value. The authors reported that the curve was exponential. The observed frequency shift had reached 90% of its final value within 0.2 seconds.

Referring now to FIG. 4, a top view of an alternate embodiment of the subject device is illustrated. Here, four interdigitated capacitors are detailed; interdigitated capacitors 11 and 31 repeated along with added interdigitated capacitors 71 and 81, all located on the one substrate 10. While all interdigitated capacitors might be of similar construction as concerns the interdigitated fingers and the first coatings of silicon nitride there may be some circumstances where different construction may be desired in order to bring the capacitances to near balance. In the embodiment shown in FIG. 4, interdigitated capacitor 11 utilizes an outer coating 20 comprising a compound preferentially sensitive to one constituent gas present in the mixture of gases under consideration, such as to gases commonly used in anesthesia procedures, for example, a halogenated hydrocarbon such as halothane. For such a halogenated hydrocarbon, a compound to be utilized for this outer coating 20 of interdigitated capacitor 11 would be General Electric Silicone Rubber RTV 615A.

Next, second coating 40 on interdigitated capacitor 31 is selected to be the same as coating 20 of interdigitated capacitor 11 or other material which exhibits similar thermal properties relative to change of capacitance as does the second layer coatings of the plurality of interdigitated capacitors on substrate 10. The coating 40 is followed by glass plate 42. As earlier discussed, this interdigitated capacitor will be indicative of the change in the capacitance due to temperature changes only.

Next, outside layer 70 of interdigitated capacitor 71 is chosen to be preferentially reactive to one of the other constituents of the gas mixture environment, such as in the example of gases useful in anesthesia procedures, nitrous oxide. In such cases, outer layer 70 then comprises a material such as Dow Silicone Rubber DSR 319 or General Electric type GE 4524 U-100. These materials were selected because they exhibit the same or similar processes as do the compounds used for sensing halothane, which is believed to be the absorption of the specific gas causing a resultant swelling.

Lastly, outer coating 80 of interdigitated capacitor 81 comprises a material sensitive to one of the other constituents of the gas mixture desired to be sensed and measured, for example, water vapor which might be present. In such a case, coating 80 comprises a material such as Dow Silicone Rubber DSR 515 B, also selected because it exhibits the same preferentially absorptive or permeability characteristics above, but for water.

As indicated in FIG. 4, all interdigitated capacitors have a set of leads running to the opposite end of substrate 10 for electrical attachment to the appropriate electronics to indicate the presence of and relative level of the gases in the gas mixture.

Now there may be situations when, for example, two of the constituent gases in the environment are different but closely related. This might happen in the anesthesia system suggested where two different types of halogenated hydrocarbons are employed, although this is not the usual situation. In this situation, the preferable embodiment is to utilize different highly selective permeable membrane materials as the second covering or coating on different interdigitated capacitors. These selectively permeable membranes would be permeable only by that specific gas desired to be detected and quantitated in the environment. However, the most usual situation existing in selectively permeable membranes is that membranes permit entrance to more than one related environment gas, but each in a different, but known manner. One of the selective permeable membranes will absorb two gases in different proportions than will a second permeable membrane. Similarly, the second permeable membrane will absorb the second gas preferentially over the first gas, but the first gas will also be absorbed. Since the permeability of one gas over another through each of the selected permeable membranes is known or can be determined easily through tests, such may be compensated as will be understood by one knowledgeable in the art, such as by a microprocessor with a look-up table. This permits extrapolation and cancellation of the minor gas effect for each material and thus permits a display reading each major reaction. The microprocessor, in utilizing a look-up table refers to the table for a value which then is correlated to the true value of the major gas.

Since different silicone rubbers are permeatated by different anesthesia gases in different known manners, it is readily apparent that by comparison of the outputs of two different interdigitated capacitors, the type of gas detected can be determined. Similarly, if the operator is expecting to detect and measure one gas and another is indicated, such information is readily made apparent to the operator who may then correct the error and place the proper gas into the system.

Further, it may also be desirable to detect and measure the concentration of a third anesthesia gas in the anesthesia system, such as nitrous oxide. Material coatings sensitive to nitrous oxide are also sensitive to halogenated hydrocarbons, although the relative effects of each gas are known. The process of minor gas effect cancellation is easily accomplished through known techniques in the processing of the signals in the electronic circuits such as shown in FIGS. 3 or 5. For instance, there are techniques for handling it in signal processing. One possible technique is as described above employing look-up tables. In addition, it would be possible to use polynominal approximations, or process of cancelling or differencing, or of simultaneously solving mathematical expressions setting out the known relationship of the major and minor gas effect.

Referring now to FIG. 5, a schematic block diagram of the proposed electrical circuitry for utilizing different interdigitated capacitor pair sets in a system such as an anesthesia system to detect and determine the concentration of four constituent gases is detailed.

First, similarily to the system shown in FIG. 3 is readily seen in that the same or similar electrical and mechanical elements are used as in FIG. 3. The electrical signal from oscillator 51 is fed back to amplitude stablizer 55 and is also directed to the first of a series of the same or similarly constructed balanced diode-quad detectors 53a-d, the output of each being directed to a pair of interdigitated capacitors as shown. Reference to each of these interdigitated capacitors immediately follows a brief description of the remaining elements.

The output of each of the balanced diode-quad bridge detectors 53a-d is directed to each of a series of low pass filters 57a-d, and then on to DC amplifiers 59a-d as was the case in FIG. 3. From there, the signal from each DC amplifier 59a-d is directed to multiplexer 71 which receives the varying dc signals indicative of capacitance change in each interdigitated capacitor pair sensed. The multiplexer 71 timing is controlled by the microprocessor program so that each dc signal is processed by the analog to digital converter 72 sequentially one at a time.

The analog to digital converter 72 changes the relative dc voltage from a specifically interrogated interdigitated capacitor pair into a digital word representative of the interrogated voltage. Microprocessor 73 has previously been programmed with the proper mathamatical procedures determined by known techniques from available response curves of each of the material coatings to the particular gas or gases it is primarily selectively responsive to. The nature of the microprocessor program is to sample each interdigitated pair and then compensate the appropriate data sets for zero offset, nonlinearities or other specific artifacts such as baking out humidity effects on the sensors used for the specific detection of the anesthesia gases.

From the microprocessor, the signals are directed to digital indicators 61a-d, which may be the same or similar digital indicators as utilized in FIG. 3. Each of digital indicators 61a-d will indicate a value representative of the presence and concentration of a particular constituent gas of the gas mixture in which the interdigitated capacitor pair set resides.

Still referring to FIG. 5, the interdigitated capacitors which are connected to each of the balanced diode-quad bridges 53a-d, the first set of interdigitated capacitors 82 and 83 are constructed similarily to those interdigitated capacitors described in FIGS. 1 and 2 except as follows. If it is desired that the first set of interdigitated capacitors 82 and 83 shall sense one halogenated hydrocarbon gas, then as defined in the description of FIGS. 1 and 2, the second coating of interdigitated capacitor 82 shall be that covering or layer selectively permeable to the first halogenated hydrocarbon gas. Interdigitated capacitor 83 then will be sensitive to temperature, and the second layer covering the first passivative layer shall be the same or similar membrane covered by a glass plate rendering the interdigitated capacitor unresponsive or passive to all gases in the environment, and only responsive to change in temperature.

Similarily and continuing, the interdigitated capacitors 84 and 85 of the second balanced diode-quad bridge detector will be characterized by the second coating layer of interdigitated capacitor 84 being primarily permeable by the second halogenated hydrocarbon gas and possibly minorly permeable to the first halogenated hydrocarbon gas. This of course may be also the case of the second layer coating on interdigitated capacitor 82. Similarily, interdigitated capacitor 85 shall have the same or similar second coating layer followed by a shielding glass plate thereby providing a balance for interdigitated capacitor 84 in use with the balanced diode-quad bridge detector 53, reflecting a change only due to change in temperature. Similarily, interdigitated capacitor pair 86 and 87 are characterized by the separate response of interdigitated capacitor 86 to the presence of nitrous oxide permeating its second layer coating. Interdigitated capacitor 87 then, as similarily described above for interdigitated capacitors 83 and 85, has the same or similar second covering layer followed by a glass plate providing a balance for its respective balanced diode-quad bridge 53.

Finally, interdigitated capacitor pair 88 and 89 connected to their respective balanced diode-quad bridge 53 are characterized in that interdigitated capacitor 88 responds only to water vapor by means of a second layer selectively permeable coating affected only by water vapor; and interdigitated capacitor 89, like interdigitated capacitors 83, 85, and 87, having the same or similar second covering layer followed by glass plate for balancing interdigitated capacitor 88, changes only to reflect change in temperature.

Obviously then, digital indicators 61a-d will each indicate the presence and level of the four constituent gases sensed, for example, the first halogenated hydrocarbon gas, the second halogenated hydrocarbon gas, nitrous oxide, and water vapor respectively.

It is realized of course that if all interdigitated capacitors are located in proximity to each other, and there is good reason for believing this may be done for compactness of the detection system, the same results above could be achieved through the use of five interdigitated capacitors, one each for the four constituent gases to be sensed, and one for the temperature compensation for all other interdigitated capacitors, providing of course, that the effect of temperature upon the second layer covering material is the same or substantially the same as the other second layer membranes over the expected temperature range. In such cases, to avoid an excess amount of electronic circuitry to substitute a changing value of capacitance for the temperature sensing interdigitated capacitance in each of the balanced diode-quad bridges, it is necessary to place a fixed capacitor in each of the balanced diode-quad bridge detectors 53 for comparison with their respective interdigitated capacitor. Then the resulting output of the balanced diode-quad bridge detectors temperature may be compensated at the multiplexer 71 or microprocessor 73 by detecting the change in the electrical signal received from the interdigitated capacitor sensing change in temperature only.

Referring now to FIG. 6, a block schematic diagram is shown employing the subject device in a typical circle anesthesia delivery system where the inspiratory anesthetic concentration directed to the patient for breathing is monitored, and the expiratory anesthetic concentration breathed out by the patient is also monitored.

With the elements shown in FIG. 6, the anesthetist initiates the process by making preliminary adjustments on the anesthetic vaporizer 91 to inject the different constituents of gas into the system. The anesthetic gases enter the system circle, first moving to the left and passing one-way valve 95 and then to enter the patient's respiratory system. The expiratory gases exhausted by the patient then pass the second one-way valve 94 located in the return side of the circle to the point where the gas path is intersected by pop-off valve 96 and reservoir bag 93. From there, the expiratory exhaust continues to $CO_2$ absorber 97 to complete the cycle and mix with newly incoming anesthesia gases. Note that the circle system allows rebreathing of gases by the patient, but the placement of one-way valves ensures that recirculated gases must pass through the $CO_2$ absorber before reaching the patient. Note also, that the system input and output are the gas delivery system and the pop-off valve respectively. The pop-off valve 96 prevents high pressure build-ups and is itself connected to an exhaust or scavenging system (not shown). The reservoir bag 93 allows for high flow during inspiration and expiration as well as providing an indicator of spontaneous breathing and allowing assistance by the anesthetist by squeezing the bag. If a high flow is delivered by the gas delivery system, then pop-off valve 96 will be open much of the time and the rebreathed gas will make only a small contribution to the concentration of anesthetic delivered to the patient. However, if a low flow is delivered to the patient, pop-off valve 96 will be closed much of the time, and the rebreathed gas will have a significant effect on the concentration of anesthetic delivered to the patient. There are two major applications of the subject device in anesthesia gas monitoring.

When the device 1 is placed in location "A", it provides an indication of anesthetic gas concentration delivered by the gas delivery system. This use of anesthetic gas sensor device 1 provides a necessary safety check for proper function of the gas delivery system.

When the device 1 is placed in location "B", it provides an indicator of anesthetic gas concentrations inhaled and exhaled by the patient. Since water vapor is present at this location, the device 1 will be provided for such sensing. Anesthetic gas concentration measurements of inhaled and exhaled gases are useful for several reasons. As mentioned previously, when low flow rates are used, the rebreathed gases contribute to the inhaled anesthetic concentration. Therefore, it is desirable to know the difference between concentrations at "A" and "B" for optimum anesthetic management. The concentration at the end of the expiration cycle is related to the arterial blood concentration and hence to the depth of anesthesia. Thus measurements of inspiratory and expiratory anesthetic concentrations can provide the clinician with valuable information regarding the patient uptake of anesthetics. In addition, this data provides basis for calculation of endtidal respiratory volume and cardiac output. It should be noted that there are many other clinical and research applications for anesthetic gas concentration monitors.

In other experiments, it has been found possible to utilize the basic construction shown in FIGS. 1, 2a, and 2b, with the second coating upon the sensing interdigitated capacitor 11 being a membrane which will pass into its interior selected ions. An example of such is a membrane of Valinomycin. For testing purposes, both interdigitated capacitors on the substrate were utilized to sense the particular particle. In this case, a Valinomycin layer for placement upon the silicone nitride layers 18 and 38 of both interdigitated capacitors 11 and 31 was prepared by mixing 10 mg of Valinomycin with 4 ml of 5% PVC (in Tetrahydrofuran) and 0.24 ml Dioctylphthalote (DOP). The Valinomycin solution, in an amount of 2 microliters, was dropped upon each silicon nitride layer with a microsyringe. Thereafter, the substrate was placed in a dry nitrogen filled box for 24 hours.

As Valinomycin is selectively permeable to Potassium ions, and does prefer Potassium over Sodium by about two to one, a test of the sensor was performed by placing it into various concentrations of NaCl and KCl made by diluting known standards. Six ml of separate NaCl and KCl solutions were placed in mini-breakers and the substrate inserted. Results were recorded starting with the most dilute solution first. The temperature of all solutions was made equal and kept constant in all tests. By careful monitoring of the solution temperatures, it was possible to replace the usual temperature sensing interdigitated capacitors with external variable capacitors in the balanced diode-quad circuits. This was done for both interdigitated capacitors on the substrate. The tests were then repeated under the same conditions utilizing a second pair of interdigitated capacitors prepared the same way and the same test solution used. These results are labeled as Test II.

| Standard Solutions | | TEST I Interdigitated Capacitor | | TEST II Interdigitated Capacitor | |
|---|---|---|---|---|---|
| | | 11 | 31 | 11 | 31 |
| 100 mM | NaCl | +1.3159 | +1.4130 | +1.4281 | +1.4288 |
| 10 mM | NaCl | −1.3818 | −0.8985 | −1.4098 | −1.4171 |
| 6.6 mM | NaCl | −1.4012 | −1.0902 | −1.4202 | −1.4253 |
| 5 mM | NaCl | −1.4080 | −1.2600 | −1.4248 | −1.4288 |
| 3.3 mM | NaCl | −1.4141 | −1.3515 | −1.4288 | −1.4321 |
| 1,67 mM | NaCl | −1.4202 | −1.3943 | −1.4337 | −1.4355 |
| 1 mM | NaCl | −1.4228 | −1.4044 | −1.4340 | −1.4355 |
| 100 mM | KCL | +1.4025 | +1.4377 | +1.4549 | +1.4546 |
| 10 mM | KCL | −1.3470 | −.7350 | −1.3958 | −1.4061 |
| 6.6 mM | KCL | −1.3919 | −.9721 | −1.4145 | −1.4214 |
| 5 mM | KCL | −1.4023 | −1.1590 | −1.4219 | −1.4272 |
| 3.3 mM | KCL | −1.4110 | −1.3012 | | |
| 1.69 mM | KCL | −1.4175 | −1.3883 | −1.4321 | −1.4343 |
| 1 mM | KCL | −1.4218 | −1.4009 | −1.4337 | −1.4354 |
| DI | H$_2$O | −1.4245 | −1.4115 | −1.4358 | −1.4372 |

Within approximately two seconds after the interdigitated capacitors had been immersed in each respective solution, the values recorded were reached. The results above are relatively linear from the very weak solutions to the solution strength of 10 mM of NaCl and KCL, going from the greatest negative towards a zero value. Between 10 mM solution strength to 100 mM of NaCl and KCL, the results cross the zero voltage value to a positive value.

It is also obvious that there are many variations of Applicant's device which reside in the basic invention wherein the presence and concentration of gases, particles, molecules, compounds, or the like, in other fluid environments which may be detected and concentration measured.

For example, referring now to FIG. 7, apparatus is shown for detection and measurement of concentration of various ions in sample solutions. More specifically, apparatus 100 shown in cross-sectional view in FIG. 7 details container 102 constructed having two wells to contain the various constituents of the apparatus. On one side of the container is a well of known volume filled with a fluid 104, such as deionized water, adapted to receive the ion to be detected, the fluid surrounding the interdigitated capacitors 106 and 108. These interdigitated capacitors represented as squares have the same preliminary base construction as disclosed earlier, i.e., the substrate, the electrically conductive metallic strips upon the substrate which form the plates of the capacitor, and the first passivated insulation layer covering the metal conductive capacitor plates upon the substrate. The substrate is so positioned that the electrical leads 110 and 112 connecting with the interdigitated capacitors emerge from the well for connection to the electronic capacitance measuring instruments as described in FIG. 3. The usual second covering is not placed upon the interdigitated capacitor 106 first covering, but instead at a distance as detailed below. Interdigitated capacitor 108 was however covered with a second coating material impervious to the fluid, for example, an epoxy.

Separating the two wells of liquid is an ion selective membrane 114 which is not permeable to the deionized water, but is permeable to one or more selected ions. The ion selective membrane 114 is replacing the usual second layer of interdigitated capacitor 106 as mentioned above. The membrane is placed in a liquid-tight relationship with the sides of the container 102 to prevent fluid leakage between the wells. In communication with membrane 114, but opposite the deionized water is the sample solution 116 which contains, or is believed to contain, the ion or ions which are desired to be detected and concentration measured.

Lastly, a pair of electrodes 118 and 122 are connected to a voltage source, electrode 118 connected to the positive pole of battery 120 and electrode 122 to the negative pole of battery 120. As shown, electrode 118 is in electrical communication with the sample solution 116 and electrode 122 the deionized water 104. The purpose of the electrodes 118 and 122 connective with their battery 120 is to place an electrical potential across the two fluid solutions, 116 and 104, in order to electrically attract ions of the proper polarity (here positive) through the ion selective membrane 114, providing of course, the ions are of the type passed by membrane 114. Obviously, this is a means to accelerate specific ions from the sample solution 116 into the deionized water 104. Natural migration would also occur in absence of an electric field, however, this can take an extremely long time.

Upon the movement of the specific ions from solution 116 into solution 104, the dielectric constant of the liquid surrounding the interdigitated capacitor 106 will be changed from a fluid free of ions into a fluid with specific ions in solution. Such a change in the capacitance of interdigitated capacitor 106 due to the change of the dielectric constant of the fluid immediately surrounding interdigitated capacitor 106 is detected by the electronic apparatus attached to leads 110 and 112 and detailed in schematic block diagram of FIG. 3. The epoxy coating on interdigitated capacitor 108 serves to keep the deionized water with the ions in solution sufficiently far away that the ions do not affect the electric field in the capacitor dielectric, and thus any changes in its capacitance will be due to changes in temperature.

Tests have been conducted utilizing the above embodiments for sensing the presence of and measuring the concentration of Sodium and Potassium ions using solutions of Sodium Chloride and Potassium Chloride for solution 116 as follows. Since no second material layer was placed over the silicon nitride of interdigitated capacitor 106, the membrane 114 acted as the necessary particle selective mechanism for permitting the particular sought ions to come into proximity of the interdigitated capacitor 106 electric field.

Membrane 114 was prepared to pass Potassium ions by permitting a solution containing Valinomycin to dry upon a cellulose acetate sheet sealed in liquid-tight fashion to the sides of the container 102 with an appropriate non-reactive, passive adhesive. The Valinomycin membrane was prepared by mixing together 10 mg Valinomycin with 4 ml 5% polyvinyl chloride (in tetrahydrofuran) and 0.24 ml Dioctylphthalate (DOP). The solution was placed on the cellulose acetate and allowed to dry for 24 hours.

The interdigitated capacitor 108 which has the silicon nitride covering followed by the epoxy covering reflects only change in capacitance due to changes in the temperature of the environment solution 104 and is used as a correction factor for the change of capacitance of interdigitated capacitor 106 due to temperature effects while it senses the added charged ions in the surrounding dielectric material.

Silver wire electrodes 118 and 122 were coated with Silver Chloride. Equal volume solutions of NaCl and KCl were each prepared to a concentration of $10^{-2}$ molar. The solutions were then mixed.

The conditions of the test were that the well on each side of membrane 114 contained three milliliters of solution. The solution surrounding the interdigitated capacitor 106 was deionized water. The driving potential was 0.5 volts and the solution 104 was continually stirred.

The solution of NaCl and KCl was placed in the well shown containing liquid 116. The output reading went negative at a slope of approximately 0.018 volt per hour reaching a maximum negative value in 11 hours. Thereafter, the digital voltmenter moved positive at a slope approximating 0.020 volt per hour for approximately 20 hours.

After the tests were completed, solution on both sides of the membrane 114 were tested with a flame photometer indicating that there still remained Na and K ions in the well in which they were originally added, and that there was a predominance of K ions over Na ions in the well containing the interdigitated capacitor sensor.

The tests which were conducted upon the interdigitated capacitors utilizing ionized solutions used solutions of rather weak concentrations. It has been determined that the invention will detect and measure the concentration of ions in a highly concentrated ionized solution. However, it has been found necessary in such cases to compensate for the resultant increased capacitance, primarily because the balanced diode-quad bridge tends to saturate due to the vast difference in the capacitance of the sensing interdigitated capacitor in the presence of a large concentration of ions and the epoxy coated or otherwise modified temperature sensing interdigitated capacitor. For example, it has been determined that the capacitance of the basic interdigitated capacitor, normally in the range of 15–20 pf, may increase to as much as 200 to 300 pf in the presence of highly concentrated ions.

In order therefore to utilize the temperature compensating interdigitated capacitor in the electronic circuit which has been employed, it is necessary to modify the circuit configuration. To accomplish this, two balanced diode-quad bridges may be employed. One bridge circuit is used to monitor the temperature sensing interdigitated capacitor; the corresponding reference capacitor is a fixed capacitor of approximately the same value as the temperature sensing interdigitated capacitor. The D.C. Voltage output is then proportional to the temperature of the fluid.

A second diode-quad bridge is used in like manner with the interdigitated capacitor which measures the ionic concentration of the fluid. A standard variable capacitor, used with or without a plurality of fixed capacitors, is used as a reference capacitor for the second diode-quad bridge. The reference capacitor can be changed to approximate the value of sensing interdigitated capacitor. A D.C. voltage from the second circuit would be proportional to the concentration in the solution for a narrow concentration range.

The D.C. voltage from the two circuits can then be electronically combined so that the resultant voltage is compensated for temperature changes.

It would also be possible to utilize other types of electronic measuring circuits to electronically accomodate the large changes in capacitance.

A second method devised by the Inventors is to utilize the temperature sensing interdigitated capacitor as a fixed ion concentration reference. To that end, the temperature sensing interdigitated capacitor was surrounded with a liquid holding pod containing a fluid, either gas or liquid, having a known concentration of ions. Naturally, for this construction, the epoxy second layer on the temperature sensing interdigitated capacitor would not be present and the temperature sensing interdigitated capacitor would have a fixed value of capacitance for any one temperature. Then, this capacitance can be utilized as a reference in the balanced diode-quad circuit as a temperature sensing reference to the ion sensing interdigitated capacitor.

To that end, referring now to FIG. 9, a cross-sectional view is shown of the now modified temperature sensing interdigitated capacitor 310. Here construction of the basis interdigitated capacitor is the same as had been previously described, namely the substrate 10, the interdigitated fingers 34 and 36 formed upon the substrate, and the first insulative and passivating layer 38, nominally of silicon nitride 38.

Following that, pod 420, made of any non-porous material such as a plastic, surrounds and totally encapsulates the interdigitated capacitor and its first layer coating 38, pod 420 adapted to reside in an encircling groove 410 and adhering to substrate 10 by means of an adhesive first placed in groove 410. It is intended that pod 420 completely seal the interdigitated capacitor shown therein from the surrounding environment. Now interiorly to pod 420 is a standard or reference fluid, either liquid or gas, containing ions in solution. As such, interdigitated capacitor 310 now serves as a temperature sensing reference to the ion sensing interdigitated capacitor, it being anticipated that the interdigitated capacitor shown in FIG. 9 would be placed in the same environment as the ion sensing interdigitated capacitor, and in the same or similar construction as earlier defined, e.g., side by side on the substrate or proximate to the ion sensing interdigitated capacitor.

It is obvious that pod 420 covering material, while being non-porous, should have a relatively high thermal conductivity in order that heat may be transmitted across the pod efficiently so that fluid 400 interiorly will reflect the temperature of the surrounding environment.

It is noted that the contruction of the temperature sensing interdigitated capacitor 310 of FIG. 9 need not be confined to ion sensing applications, but in fact could be utilized in its same manner in a specific substance detection and sensing system such as in the anesthesia sensing system.

In such case, all that would need be done would be the addition of the same or similar second layer coating 40 of silicon rubber or similar substance, as shown by the dotted line in FIG. 9, and fluid 400 interiorly then to temperature sensing interdigitated capacitor 310 being a gas or liquid with a known concentration of that particular substance or material.

In all cases, adjustments to accomodate the modified temperature sensing interdigitated capacitor new capacitance is done in the electronics portion of the system.

For example, it has been determined that when utilizing the system with the interdigitated capacitors shown in FIGS. 2a and 2b, the ion, or other material, sensing interdigitated capacitor 11 will increase its capacitance over the temperature sensing interdigitated capacitor 31 with the increase of the presence of the ion or particular material. The reading then upon the digital indicator 61 may be positive, both the interdigitated capacitors 11 and 31 being approximately equal in capacitance and thereby indicating a substantially zero voltage output difference. However, if the temperature sensing interdigitated capacitor 310 has been preloaded with a fluid 400 containing ions or the particular substance to be sensed, initially the ion sensing interdigitated capacitor will have, in most instances, a smaller capacitance than the temperature sensing interdigitated capacitor and the output reading of digital indicator 61 would be negative. However, as the presence of ions, or specific material is increased around the sensing interdigitated capacitor, its capacitance will increase, making the output of the digital indicator 61 less negative and eventually, once the environment takes on the same concentration of ions or other material as fluid 400 in the pod 420 of interdigitated capacitor 310, then a zero point will be reached at which time the environment exactly matches the concentration of fluid 400.

Quite aside from using a well of deionized water to quantitate an ion, it is possible to use a fluid with a known concentration of an ion surrounding the interdigitated capacitor to quantitate a complement such as a counter-ion in the sample solution on the opposite side of the membrane. For example, the fluid with the known concentration of Potassium Chloride surrounds the interdigitated capacitor and the rate at which the Potassium ion escapes by permeating the membrane can be measured. The counter-ion on the opposite side of the membrane may be an iodine, fluorine, or bromine ion. It would be evident to one skilled in the art that the counter-ion should effectively compete; that is, if the ion surrounding the interdigitated capacitor is in the form of a compound with a counter-ion that is different from the counter-ion to be quantitated, the reaction kinetics of the two counter-ions with regard to the ion should be appropriately balanced.

Further, it is obvious from the above that pod 420 of FIG. 9 previously described may also be used to quantitate a counter-ion in a surrounding solution by using an ion permeable membrane for the pod 420. The pod would be however, placed over the ion sensing and concentration measuring interdigitated capacitor, rather than the temperature sensing interdigitated capacitor. It is also obvious that this embodiment prior to test should be stored in a container with the same fluid as in the pod to prevent escape of th e ion from the pod.

Referring now to FIG. 8, a cross-sectional view of the ion detection and concentration measuring device of FIG. 7 is shown in a slightly modified embodiment to show a device which may be suspended into a container filled with a solution which is to be tested for a specific ion. In FIG. 8, starting at the top, circular disk 130 is shown in cross-section having firstly at its outer periphery, electrically conductive annular ring 132. Outside of annular ring 132 is ion selective membrane 134 which in its embodiment takes substantially the shape of an open-mouthed bag, an open container, a cup or the like. The purpose is to provide a holding means for a known volume of fluid 138, such as deionized water, interiorly to the bag together with the interdigitated capacitors, the membrane bag being sealed then at its mouth against any surrounding solution. This membrane resides on the outer periphery of inner annular ring 132, which then is encompassed at the area of annular ring 132 by an electrically conductive outer annular ring 136. The relationship between the inner peripheral surface of outer annular ring 136, the sides of the membrane bag 134, and the outer peripheral surface of annular ring 132 is such as to place the connection in a water-tight configuration holding the deionized water interiorly to membrane bag 134.

Continuing, interiorly to membrane bag 134 to deionized water 138 which fills the bag completely. Attached to the underside of circular disk 130 is the interdigitated capacitor substrate 140 which has in this example two interdigitated capacitors 142 and 144 located thereon. Again the construction of the interdigitated capacitors 142 and 144 follows the construction used in FIG. 7, namely that the interdigitated capacitor 142 is first covered by a first thin passivating layer of silicon nitride so that it is still receptive to any free-floating ions which may infuse into the deionized water 138, while the other interdigitated capacitor 144 is covered with a second epoxy coating completely impervious to the resulting solution surrounding it. This epoxy layer covers the silicon nitride layer immediately below it and as a result interdigitated capacitor 144 senses only capacitance changes due to temperature.

Penetrating through the circular disk 130 are the leads to each of the interdigitated capacitors 142 and 144 as well as the electrical leads connecting annular ring 132 and annular ring 136 to the electrical battery 146 potential. Again here an electrical potential is placed across the membrane, which of course must be electrically non-conductive, in order to accelerate correct polarity ions through the membrane from the surrounding solution and into deionized water 138. It is realized that the ion selective membrane 134 must be impervious to water and to solution surrounding the bag since to be otherwise would permit the deionized water 138 stored interiorly to leak out at all times, both during storage of the apparatus and during the test times.

Clearly, although the invention has been demonstrated for sensing certain materials in two fluids, the invention may be utilized with other types of membranes such as lipid bilayer and the like to sense a variety of substances in a variety of fluids as would be obvious to one skilled in the art.

It is realized of course that the capacitors which have been shown and described in the embodiments have been interdigitated type capacitors situated upon a flat insulative substrate. However, it is obvious that interdigitated type capacitors of the type described above are not the only capacitors which may be utilized since the embodiment of the invention is the change in capacitance between the electrodes of the capacitor by the influx of the specific material into the dielectric material of the capacitor. In addition, it is also obvious that the capacitors which may be utilized in the invention need not have two electrodes creating the electric field but may have two or more electrodes creating the electric field as is well known in the art.

While a preferred embodiment of the device, together with alternate embodiments, have been shown and described, it will be understood that there is no intent to limit the invention by such disclosure, but rather it is intended to cover all modifications and alternate constructions falling within the spirit and the scope of the invention as defined in the appended claims.

We claim:

1. A capacitive detection device for sensing the presence of and measuring the concentration of a specific gas in a gaseous fluid, the device comprising:

a capacitor having a plurality of spaced apart electrically conductive electrodes, said electrodes adapted to receive an electrical input and emit an electrical output to create a capacitive electric field therebetween;

a first electrically insulative material layer passive to the gaseous fluid covering said electrically conductive electrodes; and a second material layer covering said first material layer, said second material layer being selectively permeable to the specific gas in the gaseous fluid whereby the specific gas may be sensed and its concentration measured as a consequence of its entering the electric field between said electrodes and thereby changing the capacitance between said electrodes.

2. The capacitive detection device as defined in claim 1 wherein said second material layer is a silicone rubber selectively permeable to anesthesis gases.

3. The capacitive detection device as defined in claim 1 wherein said capacitor defines an interdigitated capacitor having a pair of electrodes situate upon a flat substrate, said substrate being passive, and being impermeable to the fluid and to the specific non-aqueous material.

4. The capacitive detection device ad defined in claim 1 further comprising:

a second capacitor having a plurality of spaced apart electrically conductive electrodes adapted to receive an electrical input and emit an electrical output to create a capacitive electrical field therebetween, said second capacitor output adapted to be compared with said first capacitor output;

a first electrically insulative material layer passive to the gaseous fluid and covering said second capacitor electrically conductive electrodes; and a second material layer covering said first material layer upon said second capacitor, said first material layer and said second material layer having thermal properties similar to said first and said second layer of said first capacitor respectively whereby the output of said second capacitor is compared with the output of said first capacitor to eliminate effects of temperature upon said first capacitor.

5. The capacitive detection device as defined in claim 4 wherein said second capacitor second material layer is passive and impermeable to the gaseous fluid, and impermeable to the specific gas to be sensed and measured.

6. The capacitive detection device as defined in claim 4 wherein said second capacitor first material layer and second material layer are identical to said first capacitor first material layer and second material layer respectively, and further comprising:

an impermeable barrier covering said second capacitor second material layer whereby said second capacitor second gas layer may not be permeated by the specific material sought to be sensed and measured.

7. The capacitive detection device as defined in claim 6 wherein said first capacitor and said second capacitor define interdigitated capacitors, each said interdigitated capacitor having a pair of electrodes situated upon an insulative substrate, said substrate passive and impermeable to the gaseous fluid.

8. The capacitive detection device as defined in claim 4 wherein said second capacitor first material layer and second material layer are identical to said first capacitor first material layer and second material layer respectively, and further comprising:

a covering pod adapted to enclose said second capacitor first and second material layers, said covering pod adapted to contain a fluid having a known concentration of the specific material gas whose presence is to be sensed and concentration measured whereby said second capacitor provides a reference output for a specific concentration of the specific gas for comparison with said first capacitor output.

9. The capacitive detection device as defined in claim 1 further comprising:

a second capacitor having a plurality of spaced apart electrically conductive electrodes adapted to receive an electrical input and emit an electrical output to create a capacitive electric field therebetween, said second capacitor output adapted to be compared with said first capacitor output;

a first electrically insulative material layer passive to the gaseous fluid covering said second capacitor electrically conductive electrodes; and a covering pod adapted to enclose said second capacitor first material layer, said covering pod adapted to contain a gaseous fluid having a known concentration of the specific gas whose presence is to be sensed and concentration measured whereby said second capacitor provides a reference output for a specific concentration of the specific material for comparison with said first capacitor output.

10. A capacitive detection device for sensing the presence of and measuring the concentration of a specific non-aqueous material or a complement of the specific non-aqueous material in a fluid, the device comprising:

a capacitor having a plurality of spaced apart electrically conductive electrodes adapted to receive an electrical input and emit an electrical output to create a capacitive electric field therebetween;

a first electrically insulative material layer covering said electrically conductive electrodes; and a second material membrane spatially located from said first material layer, said second membrane communicating with the fluid and permeable to the specific non-aqueous material whereby the specific material may be sensed and concentration measured as a consequence of its entering and leaving the electric field between said electrodes and thereby changing its capacitance between said electrodes.

11. The capacitive detection device as defined in claim 10 further comprising a second fluid surrounding said capacitor first material layer, said second fluid in communication with said second material membrane to permit the passage of the specific non-aqueous material from the permeable second material membrane to the proximity of the first material layer and thereby to enter the electric field between said electrodes.

12. The capacitive detection device as defined in claim 11 wherein said first material layer defines an electrically insulative material passive to said second fluid.

13. The capacitive detection device as defined in claim 12 wherein said second material membrane is selectively permeable to the specific non-aqueous material which is to be detected and concentration measured, said second material membrane additionally impervious to said second fluid and thereby holds said second fluid in retention.

14. The capacitive detection device as defined in claim 13 further comprising:

a second capacitor also surrounded by said second fluid, said second capacitor having a pair of spaced apart electrically conductive electrodes adapted to receive an electrical input and emit and electrical output to create a capacitive electric field therebetween, said second capacitor output adapted to be compared with said first capacitor output;

a first electrically insulative material layer covering said electrically conductive electrodes; and a second material layer covering said first material layer upon said second capacitor, said second layer passive to said second fluid and impermeable to the specific material to be sensed and measured whereby said second capacitor output may be compared with said first capacitor output to detect and measure change in said first capacitor capacitance due to the presence of the specific non-aqueous material in the second fluid.

15. The capacitive detection device as defined in claim 14 wherein said first capacitor and said second capacitor defines interdigitated capacitors, each said interdigitated capacitor having two electrodes situate upon a flat electrically insulative substrate, said substrate passive to the fluid, and impermeable to the fluid and the specific non-aqueous material to be sensed and concentration measured.

16. The capacitive detection device as defined in claim 13 further comprising:

a second capacitor also surrounded by said second fluid, said second capacitor having a pair of spaced apart electrically conductive electrodes adapted to receive an electrical input and emit an electrical output to create a capacitive electric field therebetween, said second capacitor output adapted to be compared with said first capacitor output;

a first electrically insulative material layer covering said electrically conductive slectrodes, said first material layer passive to said surrounding second fluid; and a covering pod adapted to enclose said second capacitor first material layer, said covering pod adapted to contain a portion of said second fluid having known concentration of the specific material whose presence is to be sensed and concentration measured whereby said second capacitor provides a reference output for a known concentration of the specific material for comparison with said first capacitor output.

17. The capacitive detection device as defined in claim 13 wherein said second fluid contains the specific non-aqueous material which is to be detected and concentration measured, said second material membrane adapted to permit the permeation of the specific non-aqueous material from said second fluid to the first fluid whereby a complement of the specific material in the first fluid may be detected and concentration measured by measuring the change of capacitance due to the loss of the specific non-aqueous material in said second fluid.

18. A gas detection device for sensing the presence of and measuring the concentration of a specific gas in a gaseous fluid, the device comprising:

a capacitor having a plurality of spaced apart electrically conductive electrodes, said electrodes adapted to receive an electrical input and emit an electrical output to create a capacitive electric field therebetween;

a first electrically insulative material layer passive to the gaseous fluid covering said electrically conductive electrodes; and a second material layer covering said first material layer, said second material layer being selectively permeable to the specific gas in the gaseous fluid whereby the specific gas may be sensed and its concentration measured as a consequence of its entering the electric field between said electrodes and thereby changing the capacitance between said electrodes.

* * * * *